United States Patent [19]

Merlet

[11] Patent Number: 5,053,687
[45] Date of Patent: Oct. 1, 1991

[54] ARTICULATED DEVICE, FOR USE IN PARTICULAR IN ROBOTICS

[75] Inventor: Jean-Pierre Merlet, Antibes, France

[73] Assignee: Inria Institut National de Recherche En Information et en Automotique

[21] Appl. No.: 455,443

[22] PCT Filed: Mar. 15, 1989

[86] PCT No.: PCT/FR89/00112
§ 371 Date: Dec. 19, 1989
§ 102(e) Date: Dec. 19, 1989

[87] PCT Pub. No.: WO89/09120
PCT Pub. Date: Oct. 5, 1989

[30] Foreign Application Priority Data

Mar. 21, 1988 [FR] France ............... 88 03630

[51] Int. Cl.$^5$ ............................. B66F 9/00
[52] U.S. Cl. ................. 318/568.2; 318/566; 318/568.11; 901/21; 901/28; 901/29
[58] Field of Search ............. 318/560–632; 364/513; 901/3–26

[56] References Cited

U.S. PATENT DOCUMENTS

| | | | |
|---|---|---|---|
| 4,300,362 | 11/1981 | Lande et al. | 901/28 X |
| 4,732,525 | 3/1988 | Neuman | 901/32 X |
| 4,765,795 | 8/1988 | Rebman | 901/21 X |
| 4,806,068 | 2/1989 | Kohli et al. | 901/23 X |
| 4,819,496 | 4/1989 | Shelef | 901/29 X |

Primary Examiner—Paul Ip
Attorney, Agent, or Firm—Toren, McGeady & Associates

[57] ABSTRACT

An articulated device includes two plates (PI, PS) interconnected by six link members (OLij) disposed in a closed latticework structure, and a control assembly for controlling the relative positions of these two plates. Each link member is of substantially constant length and the control assembly also includes six slider members (OCij) respectively connected to the six link members (OLij) and to the bottom plate (PI), each slider member being suitable for sliding relative to the bottom plate (PI) along a predetermined sliding direction under drive from a motor (MOTij, TFij).

17 Claims, 6 Drawing Sheets

ARTICULATED DEVICE, FOR USE IN PARTICULAR IN ROBOTICS

The invention relates to an articulated device of the type comprising two plates interconnected by articulated segments shaped to form a closed latticework structure together with a control assembly for controlling the relative positions of the two plates.

In the prior art, such a device is referred to as a "parallel manipulator" and it generally possesses six segments of variable length articulated on the plates via universal joints, together with a control assembly which enables up to six degrees of freedom to be obtained for one plate relative to the other. The device is particularly suitable for use in robotics where it may constitute, for example, the end of a robot arm for insertion or assembly purposes, or it may constitute a structure fixed to a stationary platform for facing a robot arm. In this application the device constitutes a "left hand" for the robot facing it. In all cases, the device should enable complex tasks to be performed of fine assembly, precision machining, or contact monitoring of surfaces.

A device of this type may also be used in dynamic motion simulators, e.g. flight simulators or other vehicle control simulators.

French patent application number 83 12263 describes a device of this type which comprises two plates interconnected by six pneumatic actuators constituting actuators which are articulated both to the top plate and to the bottom plate, and which are controlled by electrically controlled valves. This type of manipulator has inherent natural elasticity due to the pneumatic actuators and it is most advantageous for robotics by virtue of its high position accuracy and of the ease with which force measurement may be integrated. However, such a device is relatively bulky and has relatively high mass and inertia in its moving parts, thereby limiting its speed of displacement. This considerable bulk is related to the presence of the actuators for driving the articulated segments and these also limit the working space of the device because of their diameter. Finally, the pneumatic actuators expend energy even when the top plate is not moving.

A document by Jean-Pierre Merlet entitled "Parallel Manipulator, Part 1: Theory, Design, Kinematics and Control", INRIA Research Report, No. 646, March 1987, and referred to herein as the Merlet Document describes a device which is more specifically intended to provide "left hand" functions for a robot. This device is likewise constituted by two plates interconnected by segments which are articulated both to the top plate and to the bottom plate. Each segment of this device is provided with a resilient member which enables the length of each segment to modify a little under the influence of forces exerted on the top plate. The geometry of the device can thus be slightly modified under the influence of applied forces and the system is said to exhibit "passive compliance". The top plate can be moved since it is possible to control the length of each of the segments to some extent. This function is obtained by having an electric actuator in each of the segments. However, such electric actuators suffer from the drawback of being long relative to the small amount of variation in length they offer. Thus, typically, for segment length variation of no more than 5 cm, the segment length is 50 cm, thus giving rise to an overall system height of about 50 cm. This characteristic thus imposes relatively large bulk. In addition, the mass of electric actuators commercially available at present leads to a device having a relatively high total mass, about 11 kg. This is incompatible with the loading capacities of the commoner robots, and this device therefore cannot be used as the end of a robot arm for insertion or assembly purposes, for example.

The present invention remedies these drawbacks by proposing a device which, in addition to providing high positioning accuracy and heavy nominal loading, also provides greatly reduced total bulk together with reduced mass and inertia of the moving parts.

Another object of the invention is to obtain segments of minimal bulk, thereby making it possible to obtain increased working space for degrees of freedom in rotation.

Another object of the invention is to make it possible to choose the lengths of the segments freely.

Another object of the invention is to obtain passive compliance in the device, i.e. enabling the exact position and orientation of the moving plate to be calculated in spite of the displacements due to the passive compliance of the device.

Another object of the invention is to measure the forces exerted on the moving plate on a permanent basis.

The present invention therefore provides an articulated device comprising a bottom plate, a top plate, and a control assembly for controlling the relative positions of the two plates, said control assembly comprising:

three pairs of close-together articulation locations situated on the top plate;

three pairs of close-together link locations situated on the bottom plate;

six link members each having a top end articulated on a respective one of the articulation locations and a bottom end connected via a bottom articulation to a respective one of the link locations such that the two articulation locations in a same pair are connected by two link members to the two consecutive link locations which are the closest to said two articulation locations, and which belong to two different pairs of link locations; and motor means for independently varying on command the position of an articulation location relative to the bottom plate;

the device being characterized in that each link member is of substantially constant length, and in that the control assembly further includes six slider members respectively connected firstly to the six link locations and secondly via the six bottom articulations to the bottom ends of the six link members, each slider member being suitable for sliding relative to the bottom plate in a predetermined sliding direction under the drive from the motor means.

In one embodiment, all of the sliding directions are substantially parallel and substantially orthogonal to the plane containing the three pairs of link locations situated on the bottom plate.

Advantageously, each link member is suitable, under drive from the motor means, for being positioned in a circular cone whose axis is said sliding direction and whose apex is said bottom articulation.

The control assembly may include locking means for locking each slider member against rotation about its sliding direction.

The locking means may comprise top locking means at the level of the corresponding articulation location for locking each link member against rotation about an axis interconnecting its top and bottom ends, and each bottom articulation is a universal joint constituting bottom locking means.

In one embodiment, each slider member possesses threaded means, and the motor means include six endless screws respectively associated with the six slider members and respectively rotated about their longitudinal axes by six motors; in which case the threaded means of a slider member and the associated endless screw co-operate in order to allow the slider member to slide.

Each slider member preferably comprises a hollow cylindrical tube having a first end connected to the corresponding bottom articulation, and open at its other end, and in that the threaded means comprise a tapped nut firmly connected in translation and in rotation to said other end and co-operating with the endless screw.

Each hollow cylindrical tube slides in a ball sleeve connected to the bottom plate.

In one embodiment, each articulation location is suitable for defining a first top articulation having a first axis of rotation substantially perpendicular to the plane containing the three pairs of articulation locations, and a second top articulation having a second axis of rotation substantially orthogonal to said first axis of rotation and intersecting said first axis of rotation, and a third axis of rotation substantially orthogonal to both the first and the second axes and intersecting both of them, thereby providing three degrees of freedom in rotation.

The three midpoints of the three pairs of articulation locations are situated substantially at three respective vertices of a first equilateral triangle and the six link locations are situated on a circle.

In the rest position, the three points situated respectively in the middles of the three circular arcs interconnecting the two link locations in each of the three pairs are located substantially at respective ones of the three vertices of a second equilateral triangle angularly offset relative to the first equilateral through about 60° about the axis interconnecting the centers of gravity of the two equilateral triangles.

In a preferred embodiment, the two articulation locations of each pair on the top plate coincide.

The control assembly may also include detection means for detecting at least one mechanical magnitude representative of the state of the device.

Advantageously, these detection means comprise six first sensors for determining variation in the respective positions of the location of each articulation relative to the bottom plate.

The detection means may also comprise six force sensors for determining the respective forces exerted in each of the link members.

Advantageously, the control assembly includes processor means receiving information from the detection means and controlling the motor means. In order to provide the compliance of the device, the control assembly may include six resilient shock absorber members respectively connected to the six link members.

In a preferred embodiment, each first sensor is a displacement sensor, in particular a linear potentiometer connected firstly to the bottom articulation and secondly to the bottom support, with the corresponding resilient member being situated on the corresponding sliding member.

The control assembly preferably includes safety means limiting the displacement of each bottom articulation relative to the bottom plate.

Advantageously, each safety means comprises members for switching off the power supply to the motor means and also serving, after the power supply has been switched off, to brake the corresponding sliding member.

Other advantages and characteristics of the invention appear on examining the following detailed description and the accompanying drawings, in which.

Since the drawings essentially include elements which are definitive in character, they form an integral portion of the description and may be used not only to facilitate understanding the following detailed description but also to contribute, where appropriate, to defining the invention.

There follows a description of a device more particularly intended to constitute one end of a robot arm, even though, as explained above, the invention is not limited to robotics.

Figure 1:
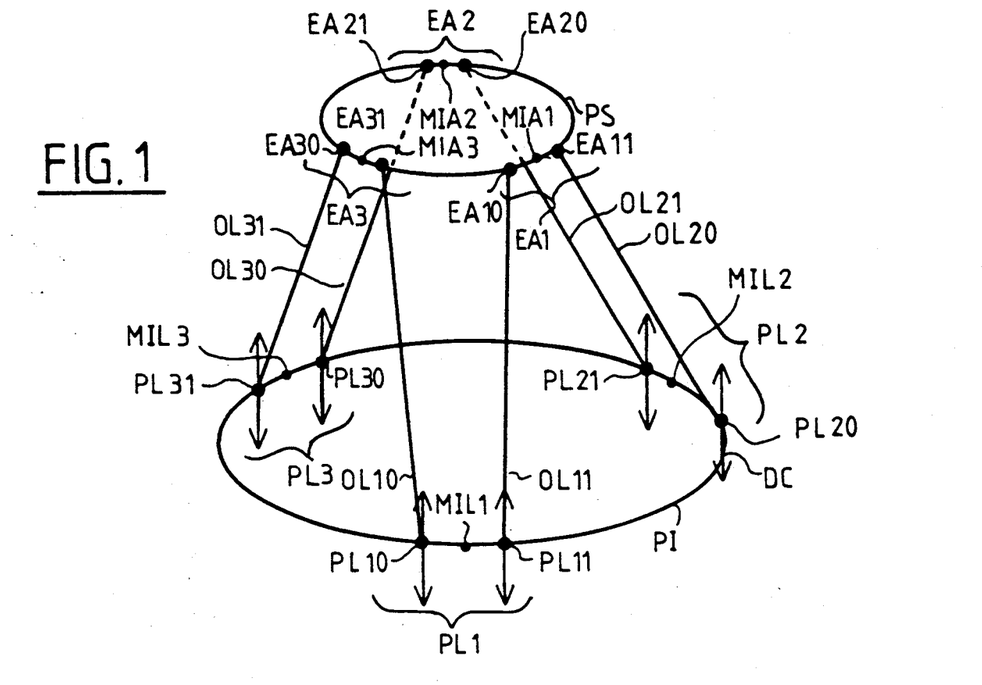
FIG. 1 is a very schematic diagram of a general embodiment of a device of the invention.

FIG. 1 shows the structure of a device of the invention in general manner. This device comprises a top plate PS and a bottom support PI which are interconnected by six link members OL10, OL11, OL20, OL21, OL30, and OL31, each articulated to the top plate and to the bottom plate. The bottom plate PI has three pairs of close-together link locations PL1, PL2, and PL3, and the top plate PS has three pairs of close-together articulation locations EA1, EA2, and EA3. Each of the six link members has a top end articulated to one of the articulation locations and a bottom end connected to a link location via a bottom articulation not shown in this figure.

In general manner, in order to facilitate understanding the references, the index i designates a pair of link locations or a pair of articulation locations, and the index j designates one of the elements in a pair i. When it is necessary to distinguish between the two elements in the same pair, they are given respective indices $j_1$ and $j_2$, and when it is necessary to distinguish two pairs, they are given respective indices $i_1$ and $i_2$.

The structure of the device of the invention is such that the two articulation locations $EAij_1$ and $EAij_2$ belonging to a pair $EAi$ of close-together articulation locations are respectively connected via link members $OLi_1j_2$ and $OLi_2j_1$ to two consecutive link locations $PLi_2j_1$ and $PLi_2j_1$ which are those closest to said two articulation locations $EAij_1$ and $EAij_2$, with these two link locations respectively belonging to two different pairs $PLi_1$ and $PLi_2$ of link locations.

Each bottom articulation corresponding to each link member is capable of sliding relative to the bottom plate along a sliding direction DC passing through the corresponding link location. In order to simplify implementation, all of the sliding directions DC are substantially parallel to each other and substantially orthogonal to the plane containing the three pairs of link locations PLi. The bottom articulations are caused to slide by means of motors (not shown in this figure).

A rest position of the device is now defined as being the position taken up when the two plates PI and PS are parallel and when no action is being or has been performed on the link members by the motor means. Thus, in this rest position, the link structure between the two plates is such that the two link members connected to the two different articulation locations in the same pair diverge towards two link locations belonging to two different pairs $PLi_1$ and $PLi_2$ of link locations. Thus, for example, the straight line interconnecting the two articulation locations EA10 and EA11, the two link members OL11 and OL20, and the straight line interconnecting the two link locations PL11 and PL20 constitute a trapezium whose large base lies on the bottom plate and whose small base lies on the top plate.

Reference is now made more particularly to FIGS. 2 to 9 which show a preferred embodiment of the FIG. 1 device.

Figure 2:
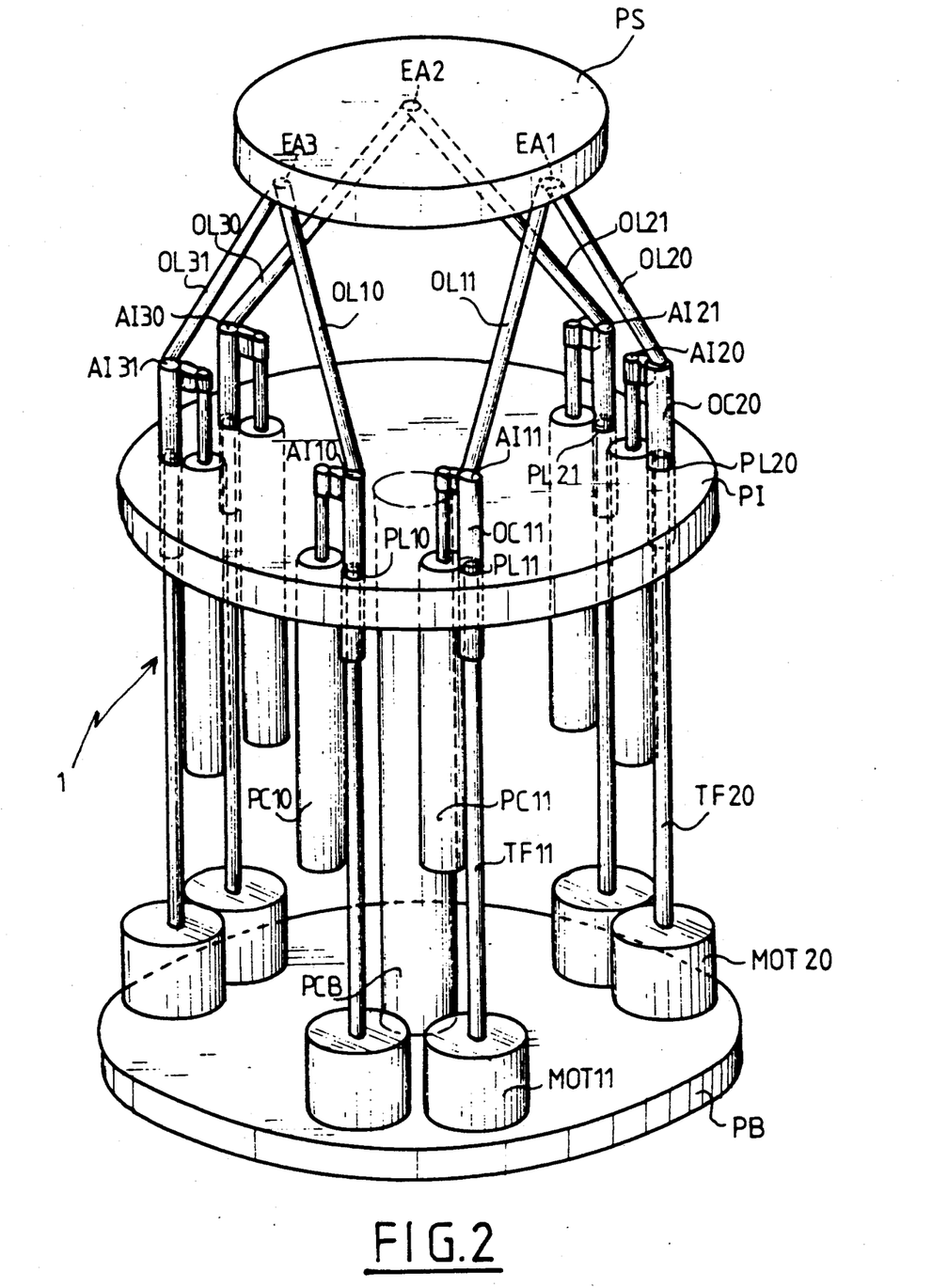
FIG. 2 is a perspective diagram showing a preferred embodiment of the device of the invention.

The top and bottom plates of the device 1 in FIG. 2 are both circular, with the top plate being smaller in diameter than the bottom plate. The device 1 also includes a base plate PS whose diameter is slightly greater than the bottom plate PI. The plate PI is situated between the plate PS and the plate PB, and the plate PB is fixed to the bottom plate PI by means of a central stand PCB. The respective centers of the three plates lie on the same straight line.

Figure 3:
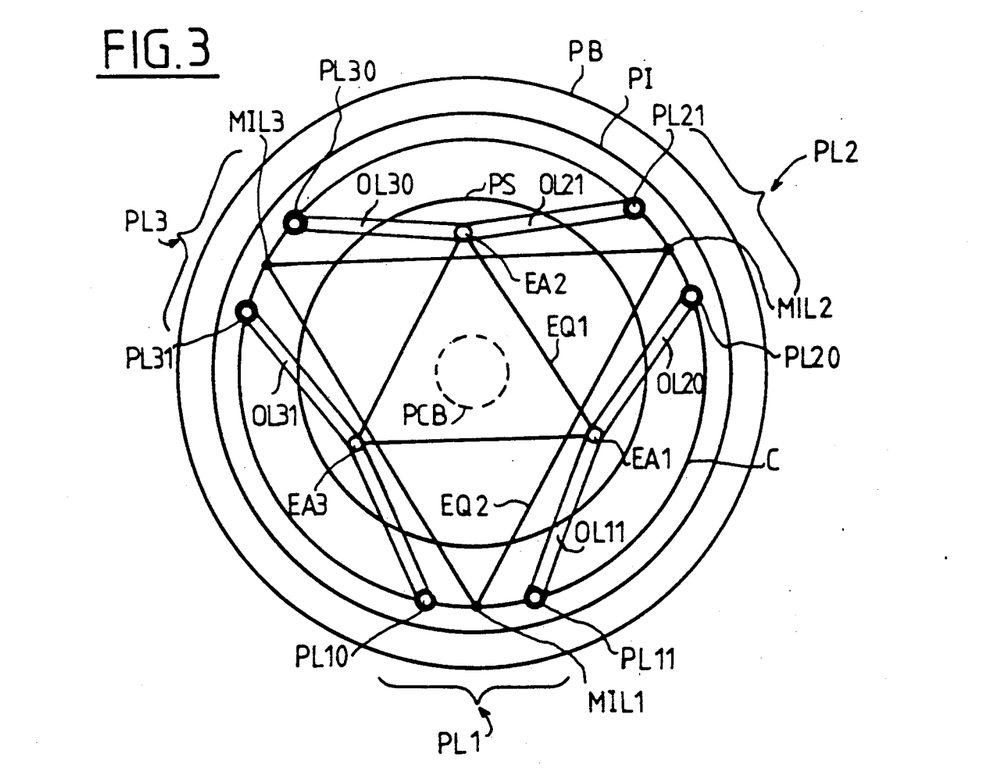
FIG. 3 is a theoretical plan view showing the main components of the device shown in FIG. 2.

With reference to FIG. 3, it can be seen that the six link locations PLij are situated on a circle C whose center coincides with the center of the plate PI. The two articulation locations in a given pair EAi happen to coincide. This disposition saves mass and simplifies the calculations for controlling the device as explained below. Thus, in the following text an articulation location is designated by the reference EAi. As a result, in this figure, the midpoints MIAi of the two articulation locations EAij of any pair EAi of articulation locations coincide and are likewise referenced EAi. The three articulation locations EAi are disposed substantially at respective vertices of an equilateral triangle EQ1 whose center of gravity is situated in the middle of the top plate. Similarly, the midpoints MILi of the circular arcs interconnecting pairs of link locations PLij are situated substantially at respective vertices of a second equilateral triangle EQ2 whose center of gravity is the middle of the bottom plate PI and which is angularly offset relative to the first equilateral triangle EQ1 through about 60° about the axis passing through the respective centers of gravity of the two equilateral triangles. Naturally, the equilateral nature of the triangles EQ1 and EQ2 described in this example is not limiting.

With reference more particularly to FIG. 2, it can be seen that a link location PLij comprises a bore in which a slider member OCij may slide, the slider member having one end connected via the bottom articulation AIij to the bottom end of link member OLij. This end of the slider member is always situated between the bottom plate and the top plate. The top end of the link member OLij is articulated to articulation location EAi. This articulation location EAi also serves to articulate a link member connected to the link location adjacent to link location PLij and belonging to a different pair of link locations.

Slider member OCij is also connected via its end close to the bottom articulation AIij to a first sensor PCij whose nature and function are explained below. This sensor PCij is securely fixed to the bottom plate in a zone close to link location PLij.

The free end of an endless screw TFij penetrates into the slider member OCij via its end opposite to its end connected to the bottom articulation AIij. This endless screw TFij has its own other end connected to a drive motor MOTij, e.g. a torque motor fixed on the base plate PB. The functions of this endless screw and of this motor are explained below. Apart from the top and bottom plates, all of the items constituting the device 1 belong to an assembly for controlling the relative position of the two plates PI and PS, and not all of them are shown in FIG. 2 in order to avoid overcrowding the drawing.

Naturally, the six subassemblies each comprising a motor, an endless screw, a slider member, a first sensor, a bottom articulation, and a link member, are all identical.

Figure 4:
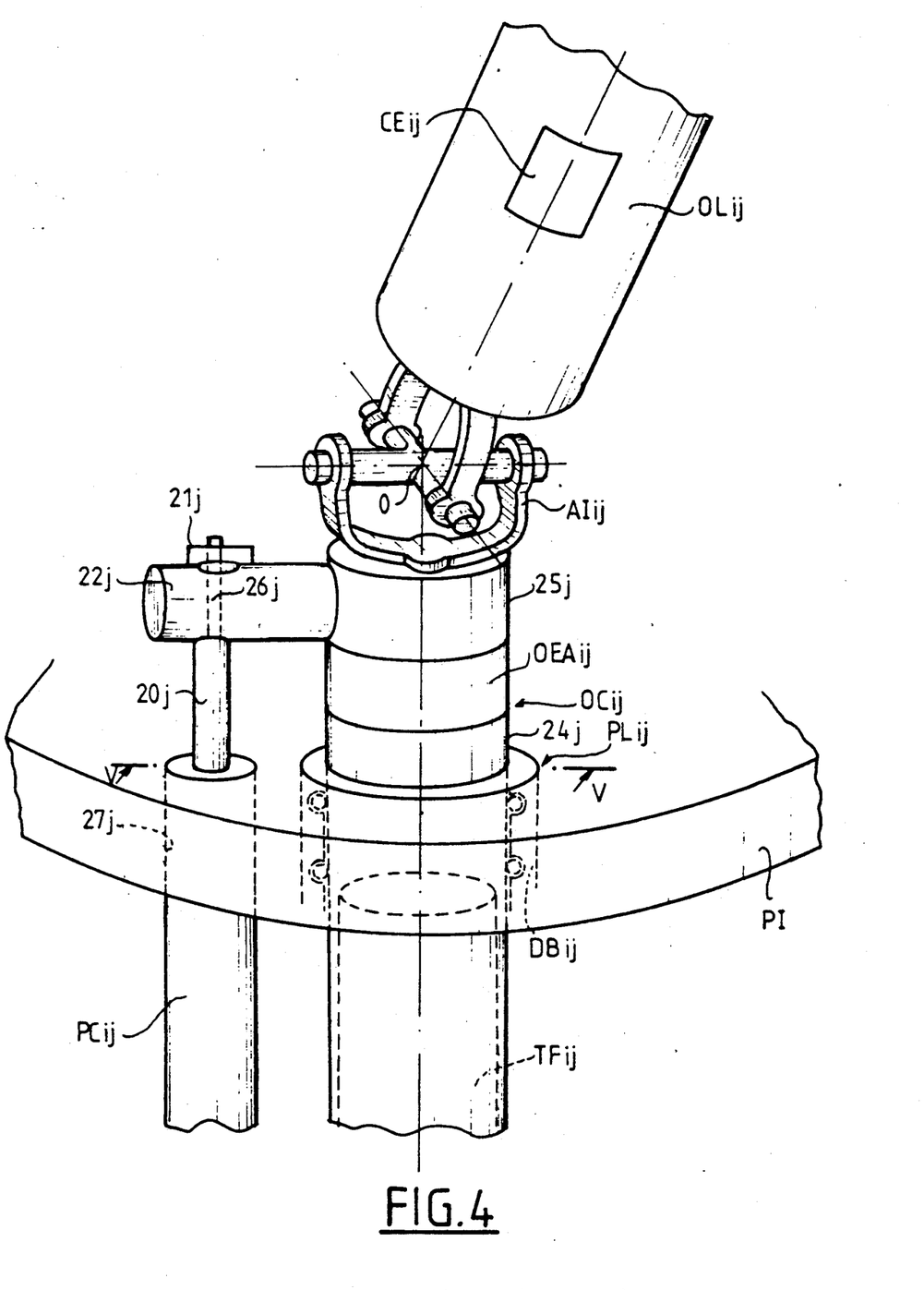
FIG. 4 is a fragmentary perspective view of a link location in the FIG. 2 device.

If reference is now made to FIG. 4, it can be seen that the slider member OCij comprises a hollow cylindrical tube 24j surmounted at one of its ends by a resilient shock absorbing member OEAij itself surmounted by a cylindrical extension 25j whose end opposite to that in contact with the member OEAij supports the bottom articulation AIij.

The link member OLij includes a force sensor CEij for measuring the magnitudes of the forces transmitted by the link member. The force sensor may be a strain gauge, for example.

The cylindrical extension 25j includes an arm 22j pierced by a cylindrical hole 26j whose axis runs parallel to the axis of the slider member OCij, and thus parallel to the sliding direction DC. The cylindrical hole 26j receives the rod 20j of the first sensor PCij which is, in fact, a linear potentiometer. This rod 20j is fixed to the arm 22j by means of a nut 21j. The sensor PCij is securely fixed in another cylindrical hole 27j of the bottom plate, close to link location PLij.

The bottom articulation AIij is a universal joint having one axis which is constantly substantially parallel to the bottom plate PI, while its other axis naturally intersects the first at a point O. The respective longitudinal axes of the slider member OCij and the link member OLij also intersect at the point O.

In order to limit sliding friction, the hollow tube 24j slides through the bottom plate PI in a ball sleeve DBij.

Figure 5:
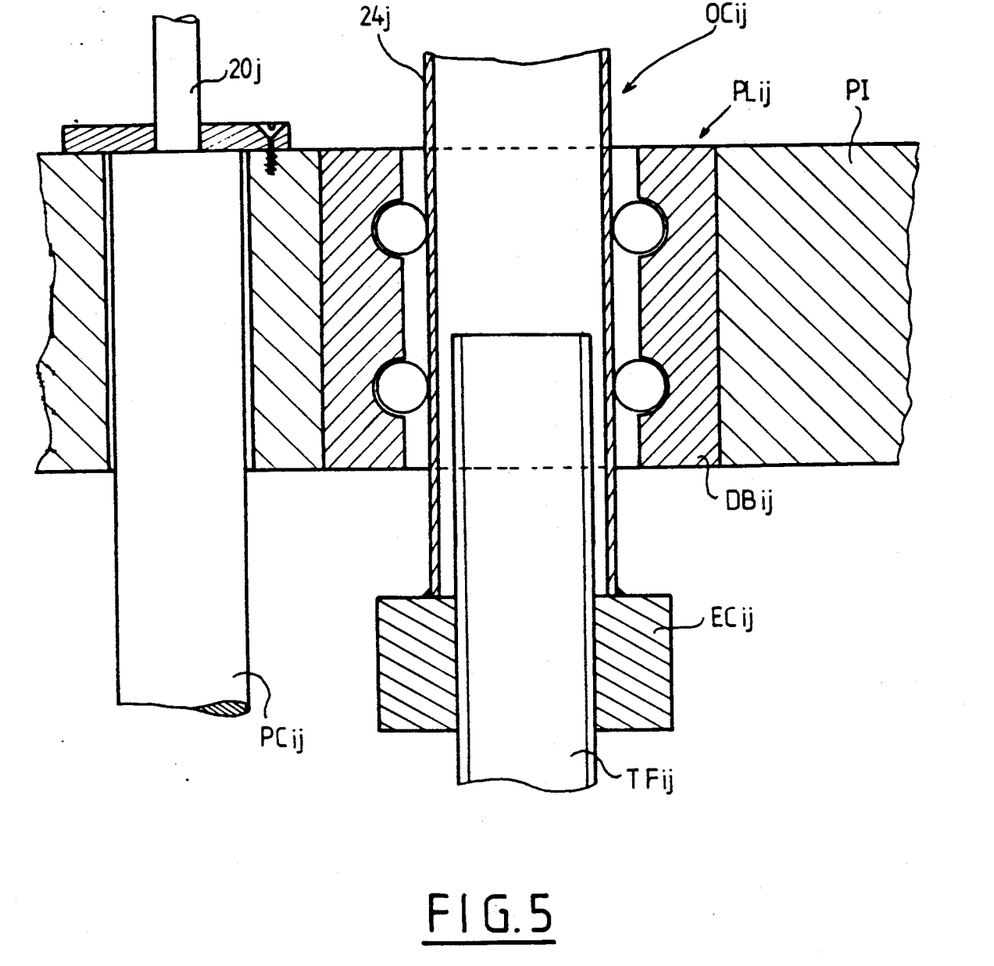
FIG. 5 is a section on V—V of FIG. 4.

The connection between the endless screw TFij and the hollow tube 24j of the slider member OCij is shown in greater detail in FIG. 5. This figure shows that the hollow tube 24j is open at its end opposite to the end which is contact with the resilient shock absorber member OEAij, and has a tapped nut ECij fixed thereto at said opening and secured against translation and rotation. The thread of the endless screw TFij cooperates with the tapping in the nut ECij which is provided with a backlash take-up member (not shown). The length of the endless screw TFij and the length of the hollow tube 24j are designed so that in operation the endless screw TFij does not come into abutment against the end of the hollow tube 24j that is in contact with the resilient shock absorber member OEAij.

Figure 6:
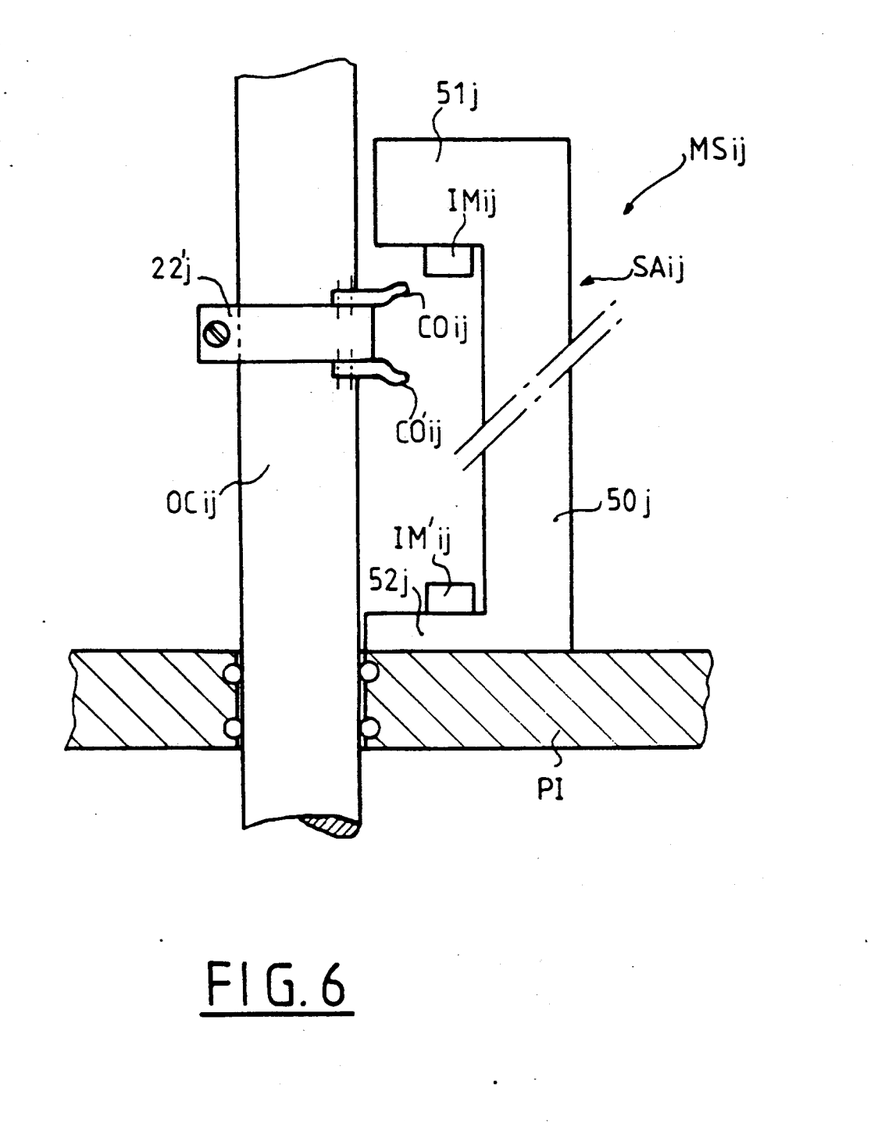
FIG. 6 is a diagram of safety means for the FIG. 2 device.

FIG. 6 is a diagram of safety means MSij associated with a slider member OCij. This safety means MSij comprises an auxiliary support SAij having a portion 50j which is substantially orthogonal to the bottom plate PI and which is extended by an extension 51j extending at right angles towards the sliding member OCij so as to be substantially parallel to the bottom plate PI. The support SAij also includes an additional extension 52j situated on the bottom plate PI and extending at right angles to the portion 50j so as to face the extension 51j. The face of the extension 51j facing the bottom plate PI includes a first magnetic switch IMij and the face of the additional extension 52j facing the first switch IMij includes a second magnetic switch IM'ij. The end of the slider member OCij situated close to the bottom articulation AIij includes an additional arm 22'j opposite to the arm 22j and provided with two spaced-apart resilient blades COij and CO'ij situated above each other. These two blades COij and CO'ij are disposed so as to make contact respectively with the extensions 51j and 52j of the support SAij. Detailed operation of the safety mechanism is described below.

Figure 7:
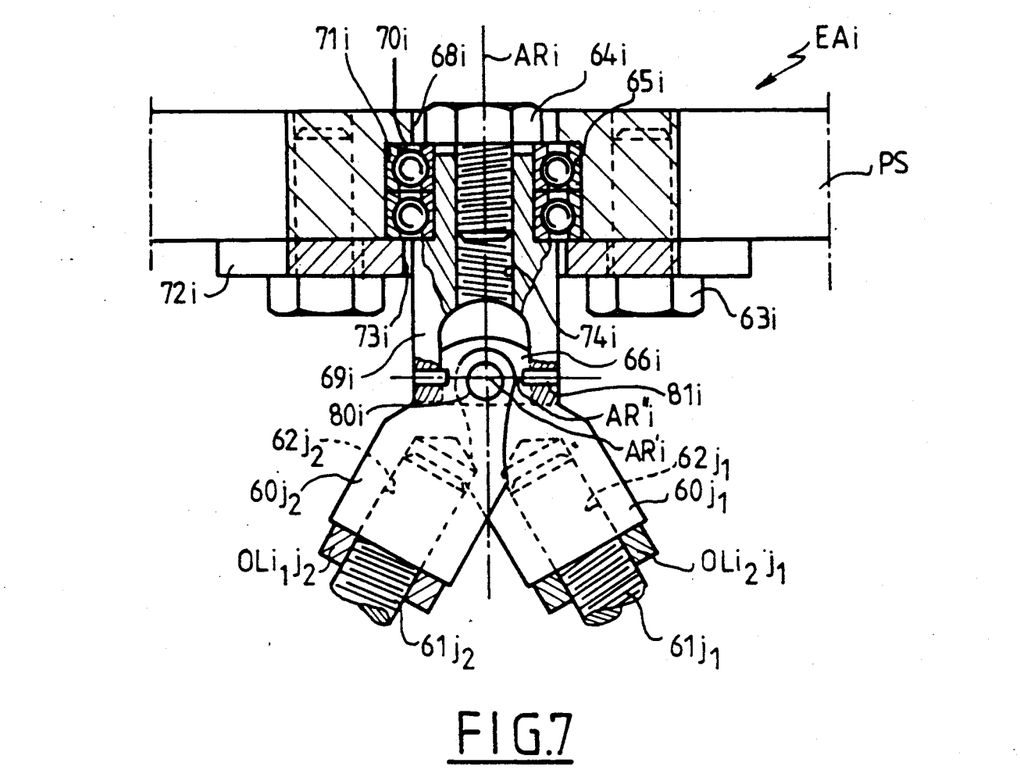
FIG. 7 is a partially cutaway elevation view of an articulation location in the FIG. 2 device.

FIG. 7 is a detailed drawing of an articulation location EAi situated on the top plate PS. The articulation location EAi includes a cylindrical hole 68i extending substantially perpendicularly to the plate PS and opening out in the top face of the plate PS, i.e. the face opposite to the face facing the bottom plate PI. The cylindrical hole 68i has a longitudinal axis ARi and is extended by an annular shoulder 70i extending at right angles away from the axis ARi and terminated by a cylindrical skirt 71i coaxial with the cylindrical hole 68i. This cylindrical skirt 71i opens out in the bottom face of the top plate PS.

The bottom face of the plate PS includes an annular plate 72i pierced by a central bore 73i disposed coaxially about the axis ARi, and having substantially the same diameter as the cylindrical hole 68i. The shoulder 70i, the skirt 71i, and the annular plate 72i serve as a support for the outside faces of two ball-bearings 65i.

The articulation location EAi also includes a body 69i whose top portion bears against the inside faces of the two ball-bearings 65i and whose bottom portion, i.e. its portion closest to the bottom plate PI, includes a U-shaped fork whose two arms run parallel to the axis ARi. The body 69i has a tapped bore 71i running through the center of its top portion and co-operating with a bolt 64i fixing it to the plate PS via the ball-bearings 51i. The annular plate 72i is also fixed to the plate PS by means of two bolts 63i. The body 69i is thus prevented from moving in translation along the axis ARi, but is free to rotate about said axis ARi.

The two free ends of the two branches of the fork of the body 69i are interconnected by a cap 66i pierced by a hole whose axis AR'i is substantially orthogonal to the axis ARi and intersects it. This hole receives a shaft 80i on which two cylindrical sleeves $60j_1$ and $60j_2$ are articulated, each having a respective longitudinal central tapped bore $62j_1$ and $62j_2$ for receiving the threaded end $61j_1$ and $61j_2$ of a respective one of the link members $OLi_2j_1$ and $OLi_1j_2$. The cap 66i is articulated to the branches of the body 69i about an axis AR"i substantially orthogonal to the axes Ari and Ar'i, and intersecting both of them.

The body 69i is therefore suitable for defining a first top articulation having a first axis of rotation ARi, the shaft 80i is suitable for defining a second top articulation having a second axis of rotation AR'i, and the shaft 81i is suitable for defining a third top articulation having a third axis of rotation, thereby providing three degrees of freedom in rotation. The overall effect of the articulation is thus of the ball-and-socket type. The fixing of the two cylindrical sleeves $60j_1$ and $60j_2$ on articulation EAi, and the disposition of the three axes of rotation ARi, AR'i and AR"i prevent any possibility of the cylindrical sleeves $60j_1$ and $60j_2$ themselves rotating about their own longitudinal axes, and the co-operation between the threads $61j_1$ and $61j_2$ with the respective tapped bores $62j_1$ and $62j_2$ contribute to locking the link members $OLi_2j_1$ and $OLi_1j_2$ against rotation about an axis interconnecting their top and bottom ends. This particular disposition of the articulation location and of the various threads constitutes the top locking means.

Since the bottom end of each link member OLij is connected to a corresponding slider member OCij via a universal joint, and since each link member OLij is prevented from rotating about an axis interconnecting its ends, the universal joint AIij prevents the slider member OCij from rotating about its sliding direction, thereby constituting the bottom locking means.

Thus, the combination of the bottom locking means and of the top locking means constitutes means for locking the slider member against rotation about its sliding direction. Naturally, other types of locking means could be provided.

The person skilled in the art will understand that the dispositions of the universal joint AIij, of the corresponding slider member OCij, and of the corresponding articulation location EAi, enable the link member OLij to be positioned in a circular cone whose axis is constituted by said sliding direction DC and whose apex is constituted by the universal joint AIij.

Figure 8:
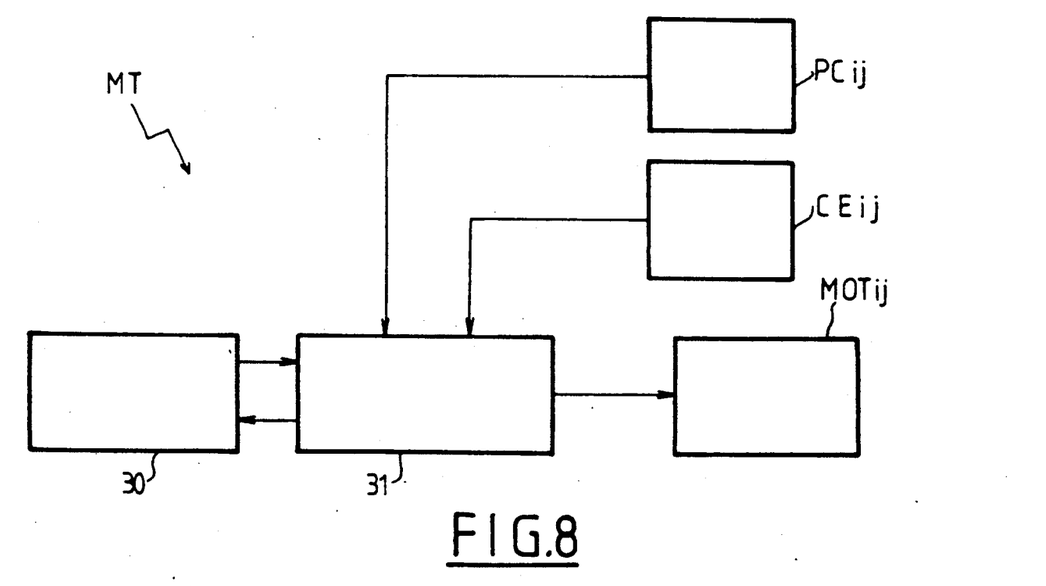
FIG. 8 is a block diagram of the processing means of the FIG. 2 device.

FIG. 8 is a block diagram of processor means for the device described above. These processor means comprise a controller 31 which receives information both from the first sensors PCij and from the force sensors CEij, and which dialogues with a central computer 30 for controlling the motors MOTij.

The device described above has a mass of about 2 kg, with each of the link members weighing about 100 grams (g). Their constant length is about 10 cm, and the dimensions of the device are such as to enable the device to be included in a circular cylinder having a radius substantially equal to 8 cm and a height substantially equal to 20 cm. The person skilled in the art will thus understand that a device has thus been implemented which is small in size and in mass and is entirely suitable for micromechanics. The absolute positioning accuracy of the device is about 10 microns and its nominal load is about 25 kg. The fact of using link members that are not motorized, confers a work space which is delimited by a displacement of 4 cm in the vertical direction and of ±4 cm laterally, due to the possibility of rotating through ±61° about the axis interconnecting the respective centers of the two plates PI and PS, and due to the possibility of rotating through ±33° about axes orthogonal thereto. This work space is considerably larger than that described, in particular, in the Merlet document.

In addition, the main mass of the device is constituted by the motors MOTij. This design is such that this mass lies beneath the bottom plate. The center of gravity of the device thus lies beneath the bottom plate and no longer between its articulated segments as in prior devices. This is most favorable for using the device as the end of a robot arm since the working load of the carrying robot is not penalized. Finally, since there are no motor means amongst the link members, they can be changed without difficulty, in order to adapt them to all types of application.

The operation of this device is now described in detail. As explained above, the object of the device is to assist in making assemblies, particularly when clearances are incompatible with the accuracy of conventional manipulators. The carrying robot brings the device into a zone in which assembly is to take place and, while holding one of the parts to be assembled, the device corrects position errors by using the information provided by the force sensors CEij. Since the device has 6 degrees of freedom, it is capable of correcting all types of positioning error.

In order to perform these displacements, the slider members move the bottom articulations AIij of the link members along their vertical sliding directions DC under control provided by the controller 31. To do this, each motor MOTij rotates the corresponding endless screw TFij. The nut ECij mounted on this endless screw and fixed to the slider member OCij moves the slider member in translation. This is possible since the slider member OCij is prevented from rotating about the sliding direction DC by the locking means. Naturally, the motors MOTij are controlled independently.

The linear displacement of the bottom articulation AIij is measured by the linear potentiometer PCij by virtue of its link to the arm 22j via its rod 20j.

This direct drive of the slider member OCij serves to reduce transmission backlash to a minimum. The motor MOTij is controlled on the basis of information from the potentiometer PCij, and the motor torque is monitored in order to apply a reference force on each link member OLij.

Conversely, if the top plate is subjected to a force, this force is spread over each of the link members OLij depending on the direction of the member. Each slider member OCij is therefore subjected to an axial force and to a radial force which is counteracted by the ball sleeve DBij. The axial force is transmitted to the resilient shock absorbing member OEAij which compresses or expands by an amount proportional to the force. The top plate therefore moves slightly, thereby providing the device with passive compliance. The displacement of the top plate is measured by the potentiometer PCij, thereby enabling the computer 30 to calculate the exact position of the moving parts. The person skilled in the art will understand that positioning the resilient shock absorber member OEAij on the slider member is particularly advantageous when compared with a resilient element that might otherwise be inserted in each link member, since the displacements due to the passive compliance can be measured accurately by the displacement sensors. In addition, the resilient shock absorber members can be replaced rapidly in order to modify the stiffness of the device.

The force sensor CEij placed on each link member OLij serves to calculate the axial force in each link member, and consequently to measure the forces exerted on the top plate during an assembly being performed by the carrying robot. The computer 30 is provided with algorithms enabling it to calculate the displacements of the top support that will enable the assembly to be performed. The motors MOTij (which in this example are torque motors) are thus controlled by force return. With this type of control, the vector of the forces acting on each articulation location is converted into a cartesian force in a system of rectangular co-ordinates which is transmitted to the computer 30 which uses the force return algorithm to calculate the cartesian X corrections to be applied to the position of the top plate. A co-ordinate transformer present in the computer 30 then calculates the corresponding lengths of the link members and transmits this information to the controller 30 which controls the motor MOTij.

Each safety means MSij serves to stop a motor when the corresponding endless screw TFij reaches its minimum or maximum stroke. The safety means switches off the power supply to the corresponding motor and applies gentle braking to the endless screw TFij. To do this, when the slider member OCij comes near to the end of its maximum stroke, the presence of the blade OCij is detected by the magnetic switch IMij fixed on the auxiliary support, thereby switching off the power to the motor. Similarly, when a slider member advances towards the base plate PB so as to bring the bottom articulation AIij towards the bottom plate PI, the presence of the blade CO'ij is detected by the second magnetic switch IM'ij which also switches off the motor power supply. The deformation of these resilient blades on the auxiliary support SAij then provides braking for the slider member OCij and the endless screw TFij. In addition, an additional switch at the controller 31 allows the safety systems to be short-circuited in order to return the top plate manually to the permitted zone.

The invention may include variants, in particular the following:

the sliding directions may be arbitrary, e.g. parallel to the bottom plate and intersecting in the center thereof, and in particular they may differ from one link location to another; and depending on the sliding direction used and/or on the types of motor means used, the person skilled in the art will be able to use various different types of bottom articulation and various different types of disposition for the articulation locations in accordance with the kinematics of the device.

Naturally, some of the means described above may be omitted in variants in which they are not useful.

I claim:

1. An articulated device comprising a bottom plate (PI), a top plate (PS), and a control assembly for controlling the relative positions of the two plates (PI, PS), said control assembly comprising:
   three pairs (EAi) of close-together articulation locations (EAij) situated on the top plate (PS);
   three pairs (PLi) of close-together link locations (PLij) situated on the bottom plate (PI);
   six link members (OLij) each having a top end articulated on a respective one of the articulation locations (EAij) and a bottom end connected via a bottom articulation (AIij) to a respective one of the link locations (PLij) such that the two articulation locations (EAij$_1$, EAij$_2$) in a same pair (EAi) are connected by two link members (OLi$_1$j$_2$, OLi$_2$j$_1$) to the two consecutive link locations (PLi$_1$j$_2$, PLi$_2$j$_1$) which are the closest to said two articulation locations (EAij$_1$, EAij$_2$), and which belong to two different pairs of link locations (PLi$_1$, PLi$_2$); and
   motor means (MOTij, TFij) for independently varying on command the position of an articulation location (EAij) relative to the bottom plate (PI);
   wherein the improvement comprises that each link member (OLij) is of substantially constant length, and wherein the control assembly further includes six slider member (OCij) respectively connected firstly to the six link locations (PLij) and secondly via the six bottom articulations (AIij) to the bottom ends of the six link members (OLij), each slider member (OCij) being suitable for sliding relative to the bottom plate (PI) in a predetermined sliding direction (DC) under the drive from the motor means (MOTij, TFij).

2. A device according to claim 1, wherein all of the sliding directions (DC) are substantially parallel.

3. A device according to claim 2, wherein all of the sliding directions (DC) are also substantially orthogonal to the plane containing the three pairs of link locations (PLi) situated on the bottom plate (PI).

4. A device according to claim 3, wherein each link member (OLij) is suitable, under drive from the motor means (MOTij, TFij), for being positioned in a circular cone whose axis is said sliding direction (DC) and whose apex is said bottom articulation (AIij).

5. A device according to claim 4, wherein the control assembly includes locking means (EAi, AIij) for locking each slider member (OCij) against rotation about its sliding direction (DC).

6. A device according to claim 5, wherein the locking means comprise top locking means (ARi, AR'i, AR"i, 62j, 61j) at the level of the corresponding articulation location (EAi) for locking each link member (OLi₁j₂, OLi₂j₁) against rotation about an axis interconnecting its top and bottom ends, and wherein each bottom articulation (AIij) is a universal joint constituting bottom locking means.

7. A device according to claim 5 or 6, wherein each slider member (OCij) possesses threaded means (ECij), wherein the motor means include six endless screws (TFij) respectively associated with the six slider members (OCij) and respectively rotated about their longitudinal axes by six motors (MOTij), and wherein the threaded means (ECij) of a slider member and the associated endless screw (TFij) co-operate in order to allow the slider member to slide.

8. A device according to claim 7, wherein each slider member (OCij) comprises a hollow cylindrical tube (24j) having a first end connected to the corresponding bottom articulation (AIij), and open at its other end, and wherein the threaded means comprise a tapped nut (ECij) firmly connected in translation and in rotation to said other end and co-operating with the endless screw (TFij).

9. A device according to claim 4, wherein each articulation location (EAi) is suitable for defining a first top articulation (69i) having a first axis of rotation (ARi) substantially perpendicular to the plane containing the three pairs of articulation locations (EAi), and a second top articulation (80i) having a second axis of rotation (AR'i) substantially orthogonal to said first axis of rotation (ARi) and intersecting said first axis of rotation (ARi), and a third axis of rotation (AR"i) substantially orthogonal to both the first and the second axes and intersecting both of them, thereby providing three degrees of freedom in rotation.

10. A device according to claim 1, wherein the three midpoints (MIAi) of the three pairs of articulation locations (EAi) are situated substantially at three respective vertices of a first triangle (EQ1).

11. A device according to claims 1 or 10, wherein the six link locations (PLi) are situated on a circle (C).

12. A device according to claim 11, wherein the first triangle (EQ1) is equilateral and wherein, in a rest position, the three points (MILi) situated respectively in the middles of three circular arcs interconnecting the two link locations in each of the three pairs (PLi) are located substantially at respective ones of the three vertices of a second equilateral triangle (EQ2) angularly offset relative to the first equilateral (EQ1) through about 60° about the axis interconnecting the centers of gravity of the two equilateral triangles (EQ1, EQ2).

13. A device according to claim 1, wherein the two articulation locations (EAij) of each pair (EAi) coincide.

14. A device according to claim 1, wherein the control assembly includes detection means (PCij, CEij) for detecting at least one mechanical magnitude representative of the state of the device.

15. A device according to claim 14, wherein the control assembly includes processor means (MT) receiving information from the detection means (PCij, CEij) and controlling the motor means (MOTij, TFij).

16. A device according to claim 1, wherein the control assembly includes six resilient shock absorber members (OEAij) respectively connected to the six link members (OLij).

17. A device according to claim 1, wherein a portion of the motor means (MOTij) is fixed to a base plate (PB) fixed to the bottom plate (PI), with the bottom plate (PI) being situated between the base plate (PB) and the top plate (PS).

* * * * *